United States Patent
Smythies et al.

(10) Patent No.: US 7,063,018 B2
(45) Date of Patent: Jun. 20, 2006

(54) METHOD AND APPARATUS FOR DETECTING THE EDGE OF AN IMAGING MEDIA

(75) Inventors: Douglas Charles Smythies, Coquitlam (CA); Christopher Earl Trautman, Burnaby (CA)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 10/756,331

(22) Filed: Jan. 14, 2004

(65) Prior Publication Data

US 2004/0231543 A1 Nov. 25, 2004

Related U.S. Application Data

(60) Provisional application No. 60/473,127, filed on May 27, 2003.

(30) Foreign Application Priority Data

May 23, 2003 (CA) .................... 2429550

(51) Int. Cl.
*B41L 3/02* (2006.01)
*B41F 5/00* (2006.01)

(52) U.S. Cl. .................... 101/486; 101/216; 101/217; 101/477

(58) Field of Classification Search ................ 101/486, 101/216, 217, 477
See application file for complete search history.

(56) References Cited

U.S. PATENT DOCUMENTS

| 4,501,507 A | * | 2/1985 | Peddinghaus | 400/134 |
| 4,572,680 A | * | 2/1986 | Kurt | 400/124.14 |
| 5,212,531 A | | 5/1993 | Monma et al. | |
| 5,519,483 A | * | 5/1996 | Kawanishi et al. | 399/45 |
| 5,649,697 A | * | 7/1997 | Kurishita et al. | 271/97 |
| 5,816,164 A | * | 10/1998 | Loffler | 101/484 |
| 5,940,106 A | * | 8/1999 | Walker | 347/104 |
| 6,247,404 B1 | * | 6/2001 | Okamura | 101/401.1 |
| 6,322,265 B1 | * | 11/2001 | Mindek et al. | 400/648 |
| 6,371,026 B1 | * | 4/2002 | Ben-Zion et al. | 101/483 |
| 6,378,977 B1 | * | 4/2002 | Gompertz | 347/19 |
| 6,435,641 B1 | * | 8/2002 | Tung et al. | 347/16 |
| 6,567,713 B1 | * | 5/2003 | Lichtenstein et al. | 700/58 |
| 6,622,625 B1 | * | 9/2003 | Sugiyama | 101/484 |
| 6,628,423 B1 | * | 9/2003 | Sasaki | 358/1.7 |

FOREIGN PATENT DOCUMENTS

EP 1081458 A3 3/2001

\* cited by examiner

*Primary Examiner*—Andrew H. Hirshfeld
*Assistant Examiner*—Marvin P. Crenshaw
(74) *Attorney, Agent, or Firm*—Oyen, Wiggs, Green and Mutala

(57) ABSTRACT

A system for determining the location of an edge of a sheet of media for alignment purposes utilizes a beam of light directed at the media surface to produce a reflected light beam. The reflected light beam intensity varies in response to the reflectivity of the surface on which it impinges and the beam position shifts in accordance with the datum of the surface at which the reflected beam is originated. By monitoring both intensity and positional information of the reflected beam as it is scanned across the media edge, the edge location can be determined using a weighted combination of the intensity and positional information.

4 Claims, 3 Drawing Sheets

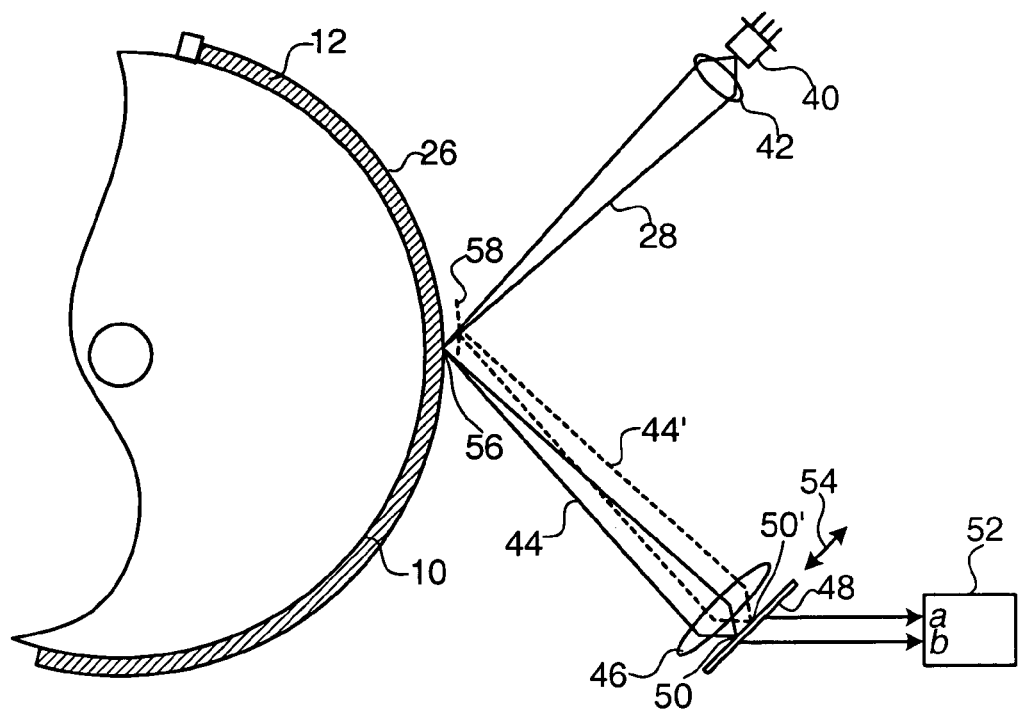
FIG. 3-A
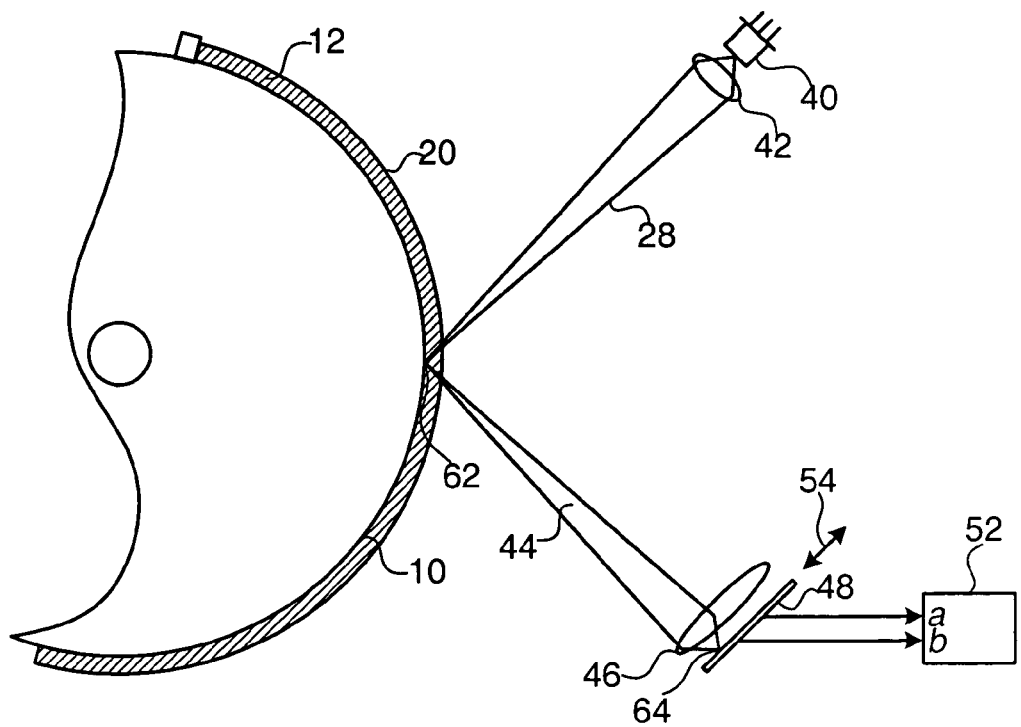
FIG. 3-B

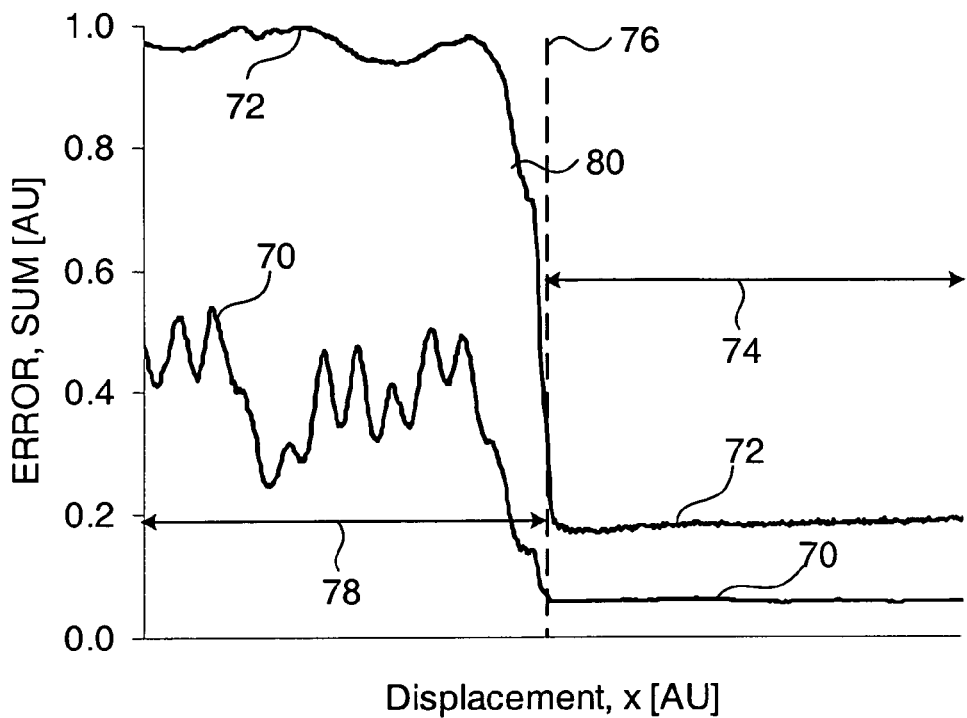
FIG. 4-A
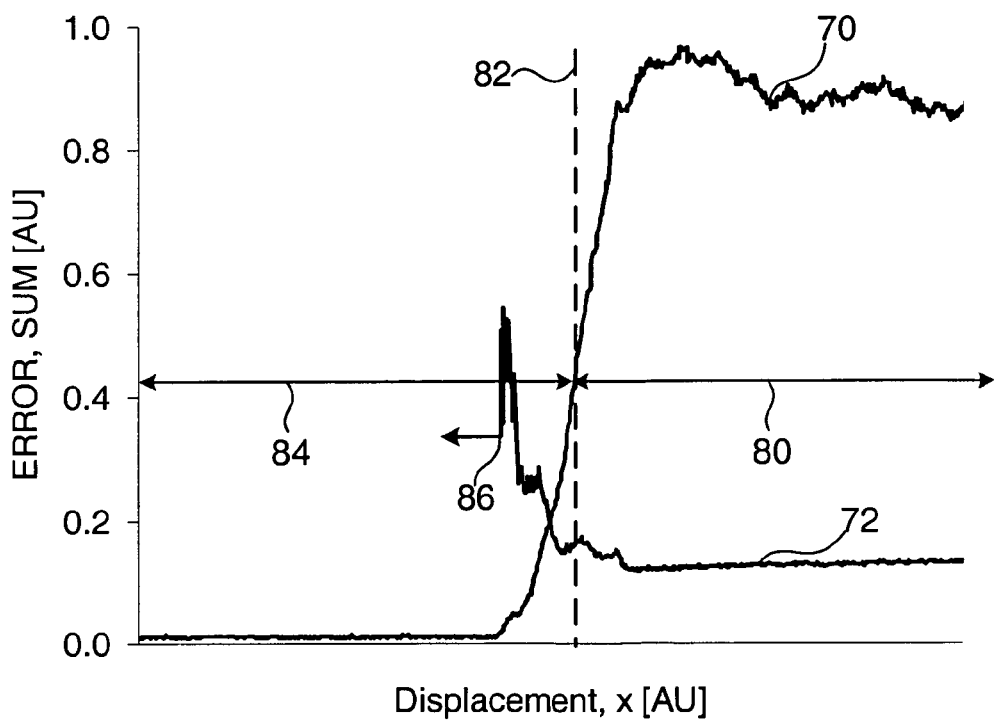
FIG. 4-B

METHOD AND APPARATUS FOR DETECTING THE EDGE OF AN IMAGING MEDIA

RELATED APPLICATIONS

This application claims benefit of the filing date of U.S. Application 60/473,127 provisionally filed on May 27, 2003 and entitled "Method and apparatus for detecting the edge of an imaging media". This application claims benefit of the filing date of Canadian Application 2429550 filed on May 23, 2003.

TECHNICAL FIELD

The invention relates to the field of imaging and more particularly to the registration of an image to the edge of a media sheet.

BACKGROUND

Most imaging systems that impart an image on a media require that the position of the media be known to some degree of accuracy so that the image is correctly positioned on the media. For example when imaging plates for the lithographic printing industry the alignment accuracy requirement is quite precise. In process colour printing, where Cyan, Magenta, Yellow and Black separations must be accurately aligned, the alignment is particularly important. It is common for a Computer-to-Plate (CTP) device to have an accuracy specification of better than ±5 μm between any two plates produced by the same device. In printing, the alignment of an image to a media is commonly referred to as "registration".

Registration of an image may be achieved by aligning to fixed stops or by optical means or a combination of the two methods. Laser based imaging systems may make use of the write laser beam, or an auxiliary laser beam, to scan over the edge of a media while monitoring the intensity of the reflected light. The edge is found where there is some transition in the reflected light level due to a difference in reflectivity between the media surface and the mounting surface. Such systems are well known in the art and are exemplified by the Trendsetter® 400 Quantum and similar devices sold by Creo Inc of Burnaby, British Columbia, Canada. In these systems the imaging media, which may be an aluminium plate, is secured to the surface of a cylindrical imaging drum. The registration in the circumferential direction is provided by a pair of registration stops disposed in the drum surface. The registration in the direction parallel to the drum axis is determined by locating the edge of the media using a low power red laser beam directed towards the imaging drum surface at an acute angle thereto. A detector, disposed to receive at least the specular portion of the reflection, is continuously monitored while the laser beam is scanned over the edge of the media. The edge location is determined on detection of a transition in the reflected signal between the media and drum surface. The drum surface is rendered at least partially absorptive at the laser wavelength in the area that the edge detection occurs to ensure sufficient contrast so that the transition is well defined.

In U.S. Pat. No. 4,518,862 to Dorn, a system for detecting the position of a sheet on a support is described. The system employs a pair of CCD line sensors that straddle the edge of the sheet. The image of the edge may be analysed using standard image processing routines to determine both angle and position. The disclosed solution is only practical in a system where the edge of the sheet is always in the same general locale. In most CTP systems a wide variety of different sized media are used and the provision of sufficient CCD line sensors to accommodate all cases would be prohibitive.

In U.S. Pat. No. 5,280,171 to Halter, a two-detector system for locating the edge of an object is disclosed. A laser beam is directed towards the vicinity of the edge at an acute angle. A first detector is located proximate the laser source. The second detector is positioned approximately over the light spot produced on the working surface. The two signals from the detectors are combined and used to determine the edge location.

In European Patent Application EP 1 081 458 A2 to Elior et al, a method of detecting the rising edge between two smooth surfaces involves focusing a beam of light on the surface closest to the source. A detector is placed so that when the beam impinges on this closest surface, very little light reaches the detector. If the beam is moved to impinge on the second surface, then the out of focus beam is reflected back into the detector thus providing a transition indicative of the rising edge between the smooth surfaces.

SUMMARY OF THE INVENTION

The present invention provides a system and method for determining the location of the edge of an imaging media based on analysis of both intensity and positional information in a beam of light reflected from the vicinity of the media edge.

In a first aspect of the present invention a method for determining the location of an edge of an imaging media is provided. The method involves directing an incident beam of light towards the vicinity of the media edge such that a reflection of the incident beam is generated and then scanning the incident beam over the media edge while monitoring the location of the incident beam in the scanning direction. The reflection of the incident beam is monitored to determine intensity and positional information. The location of the media edge is determined by evaluating the intensity and positional information.

In another aspect of the present invention a system for determining the location of an edge of an imaging media secured to a media support surface is provided. A carriage, adapted to traverse along a track, has a radiation source for directing an incident beam of light towards the vicinity of the media edge and a position sensitive detector mounted thereon. The position sensitive detector is disposed to receive a reflected beam of light from the media or support surface and to generate signals responsive to the position and intensity of the reflected beam. Means for indicating the location of the carriage on the track are provided. A controller is operably connected to the detector for receiving the signals therefrom as the carriage is traversed to scan the incident beam across the media edge. The controller is also operative to analyse the signals to derive position and intensity information indicative of the location of the media edge.

For an understanding of the invention, reference will now be made by way of example to a following detailed description in conjunction by accompanying drawings.

BRIEF DESCRIPTION OF THE DRAWINGS

In drawings which illustrate by way of example only preferred embodiments of the invention:

FIGS. 3-A and 3-B are a pair of schematic end views of an embodiment of the edge detection system of the present invention; and FIGS. 4-A and 4-B are graphically depicted examples of the signals generated in the application of the present invention.

DESCRIPTION

Figure 1:
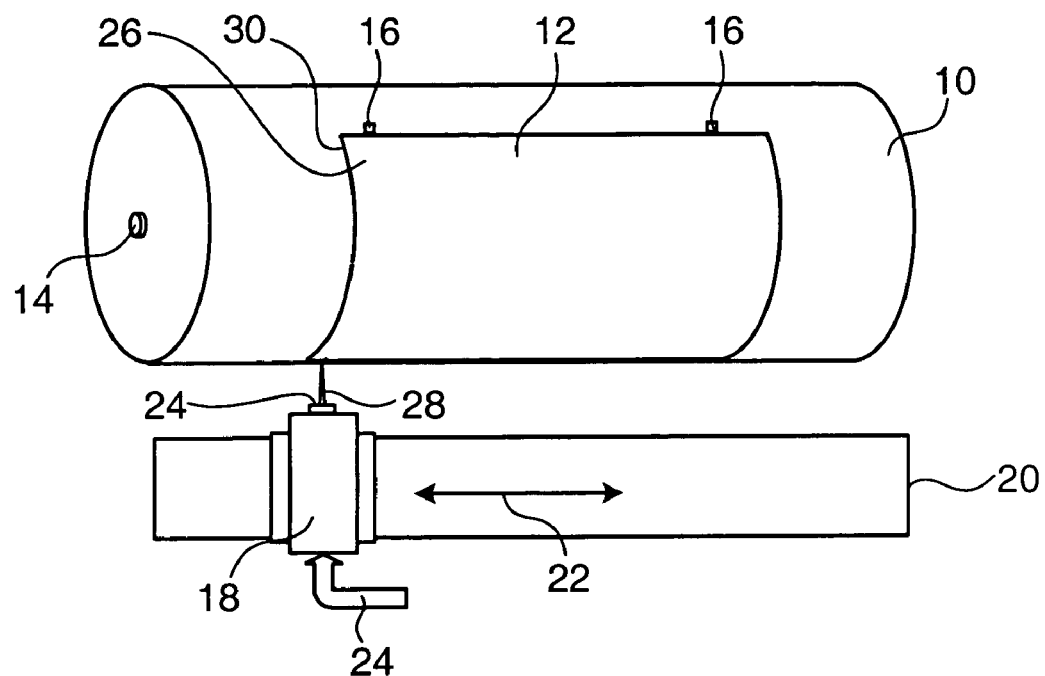
FIG. 1 is a plan view of an imaging system.

An embodiment of the edge detect system of the present invention is shown in FIG. 1. The imaging system comprises an imaging drum 10, supporting a media 12. Imaging drum 10 is rotatable about its longitudinal axis 14. The top edge of the media 12 is registered against a pair of fixed registration stops 16 and media 12 is secured to the drum. An imaging head 18, moveable along track system 20 in direction 22, is disposed to image the media 12 in accordance with imaging data supplied via data bus 24 or other means. Imaging head 18 is moved by actuation means such as a stepper motor (not shown), thus allowing accurate determination of the location of head 18 on track 20 by counting steps. The media 12 is written by an imaging beam that exits from aperture 24 and the media surface 26 is scanned by a combination of drum rotation and translation of the imaging head 18 along track 20. The edge detection beam 28 generated by the laser (not shown) is directed at the drum 10 or media surface 26, depending on the location of head 18 along track 20. The edge to be detected is shown at reference numeral 30.

Figure 2:
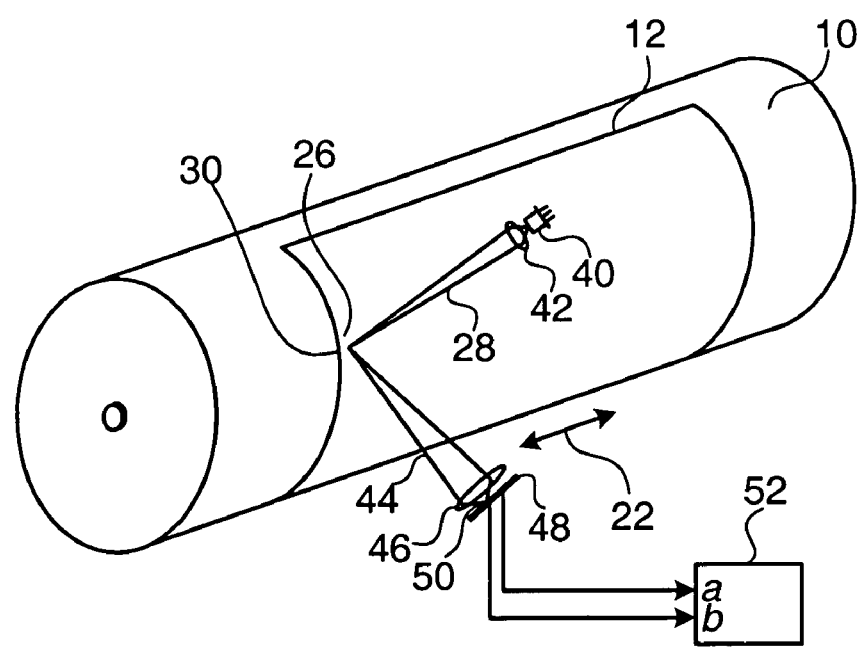
FIG. 2 is a perspective view of an imaging system showing the edge detection components to enlarged scale.

FIG. 2 shows the orientation of the beam 28. Beam 28 originates at laser source 40 and is focused by lens 42 to a spot at media surface 26. Beam 44 is reflected back from the media surface 26, collected by lens 46 and focussed onto a position sensitive detector 48 (PSD) at point 50. The laser 40, PSD 48 and lenses 42 and 46 are exaggerated in size relative to the drum 10 for illustrative purposes. Position sensitive detector 48 is of a type well known in the art, producing signals indicating both position and intensity of the light impinging thereon. PSD 48 has a substantially linear intensity response up to a certain light level. The signals from PSD 48 are coupled to a controller 52, operative to interpret the PSD signals and determine the location of the edge. Controller 52 is a microprocessor unit with a computer readable memory element for storing a plurality of data values. Laser 40 and detector 48 (and associated collection optics 42 and 46) are located on the head 18 (shown in FIG. 1).

The operation of the edge detection system is described in reference to FIGS. 3-A and 3-B showing in end view, part of drum 10 carrying media 12 on its surface as previously shown in FIG. 2. In FIG. 3-A beam 28 impinges on media surface 26 at a point 56 and is reflected back to PSD 48 at point 50. Any movement of the media surface with respect to the laser 40 and detector 48 changes the depicted situation. As an example should the media surface 26 be displaced to a position represented as a broken line at 58, beam 44 shifts to position 44' and a corresponding shift occurs at the PSD to a new location 50'. The shift to line 58 is exaggerated for purposes of illustration and is typically small, being caused by surface or drum non-uniformities. The corresponding shift at PSD 48 is sensed and interpreted by controller 52 by analysing the signals from PSD 48. The intensity of the beam at the PSD 48 will remain relatively constant as long as there is no change in surface reflectivity or other conditions and the beam 44' is focussed onto the active surface of PSD 48 without vignetting. The focusing optical elements 42 and 46 are chosen such that the beams 50 and 50' remain substantially in focus over the usual range of displacement of reflecting surface and the spot 56 at the media or drum surface does not change substantially with small changes in the distance between the laser 40 and the surface. In the situation shown in FIG. 3-A the position 50 is representative of the datum of media surface 26.

As laser 40 and PSD 48 are scanned in direction 22 towards edge 30 (shown in FIG. 2) beam 28 eventually moves off the media surface 26 and impinges on the surface of drum 10. This situation is shown in FIG. 3-B, the beam 28 now impinging on drum 10 at point 62. A corresponding shift in the position of reflected beam 44 to point 64 is detected at PSD 48 and interpreted by controller 52. Along with the positional shift of beam 44 on PSD 48, there may also be a change in intensity depending on the relative reflectivity of surfaces 26 and the surface of drum 10. Should the surface of drum 10 be more reflective than media surface 26 at the wavelength of the laser 40 then the intensity will increase. The opposite occurs where the media surface 26 is more highly reflective than the surface of drum 10.

In the preferred embodiment the PSD 48 is a lateral effect PSD, providing a pair of signals a and b to controller 52. A suitable PSD is the SL3-2 duo-lateral PSD sold by UDT Sensors, Inc. of Hawthorne, Calif. The intensity of the impinging light beam is given by the simple sum of a and b hereinafter referred to as SUM. The position is determined from the difference between a and b and is normalized by dividing the difference by the SUM to give the term hereinafter referred to as ERROR. The ERROR indicates normalized position as a number between −1 and +1 which is then scaled and calibrated to give an indication in μm. In order to increase the signal to noise ratio and improve the discrimination between the reflected signal and other spurious light, the laser 40 is sine wave modulated using a 50 kHz reference source and the signals are synchronously detected using the same 50 kHz reference source. Such techniques are well known in the art and will not be further described herein.

The translation of the beam 28 from impinging on the media surface 26 to impinging on the drum surface results in the accumulation in the controller 52 of a plurality of SUM and ERROR data points. These data points are indexed against the traversing location 22, as indicated by the count of steps provided to a stepper motor driving the carriage. The SUM signal varies according to the relative reflectivity of the surfaces. The ERROR varies with displacement of the surface generating reflection beam 44. The stored data is then post-processed to determine the exact location of the edge. FIG. 4-A graphically depicts actual signals obtained from such a system under specific conditions of media and drum reflectivity. The SUM 70 and ERROR 72 are plotted in arbitrary units on the y-axis against displacement x along track 20. In a first region 74 of the graph, corresponding to the region over which the beam 28 impinges on the media surface, the SUM 70 is relatively low corresponding to a low reflected light level. The ERROR 72 is at some relatively constant level corresponding to the media surface datum. At vertical line 76 the beam 28 starts to move off the media surface and onto the drum surface. The drum in this case is more reflective of beam 28 than the media surface and the SUM 70 increases in region 78. The fluctuation in SUM 70 in region 78 is due to the reflective nature of the drum surface which in this case was hard anodized aluminium with a mottled appearance. The ERROR 72 in region 78 rises rapidly indicating a significant departure from the media datum. The discrimination provided by the SUM signal 70 is fairly poor. Prior art systems relying only on the SUM 70, may under the circumstances shown in FIG. 4-A, have a poor discrimination accuracy for the media edge.

In the present invention the ERROR 72, corresponding to the reflecting surface datum is also monitored to provide additional information about the edge transition. The sharp transition of ERROR 72 at line 76 gives an improved indication of the location of the edge. Note that the exact point at which the edge is determined is not as important as the consistency of that determination since any small offset from the physical media edge may be taken into account through a separate calibration of the image registration. In this embodiment the edge based on the ERROR signal is determined by pinpointing the location at which the beam starts to move off the edge as indicated by the derivative of the ERROR signal (not shown). A check is made to ensure that the edge is a true edge by also looking at the ERROR. The location of the edge is then corrected by half the diameter of the laser spot size at the surface.

A different situation of relative reflectivity is shown in FIG. 4-B. In this case the drum surface is partially absorptive of the beam. SUM 70 in region 80 is high and the ERROR 72 again defines the media datum. In the region of line 82 where the beam starts to move off the media and impinge on the drum the sum drops off rapidly and has good discrimination. However, since the validity of the ERROR depends on having a sufficient SUM signal to ensure reasonable signal to noise ratio at the PSD, the low SUM in region 84 renders the ERROR indeterminate past a certain point indicated by reference numeral 86. In this situation the SUM 70 provides a better indication of the edge location than the ERROR and the edge location is primarily determined based on SUM values.

In practice, it has been discovered that an implementation of the present invention using both SUM and ERROR to determine the edge produces reasonably reliable edge detection for a wide range of different materials and conditions. The combination of SUM and ERROR is weighted to adapt to the specific situation according to the formula below:

$$x_{edge} = w \cdot x_S + (1-w) \cdot \left[ x_E - \frac{d}{2} \right] \quad \text{Eqn 1}$$

where $x_{edge}$ is the determined edge location;

$x_S$ is the location of the edge determined using the SUM alone;

$x_E$ is the location of the edge determined using the ERROR alone;

d is the width of the laser beam in the direction of motion 22.

w is a weighting factor determined according to the formula:

$$w = 1 - \frac{SUM_{min}}{SUM_{media}}$$

and $SUM_{min}$ is the minimum SUM value over a portion of the scanned range and $SUM_{media}$ is the SUM value over the media. In practice if there is an offset between $x_{edge}$ and $x_S$ d may be changed to account for this offset so that consistent results are obtained.

When the ratio of $SUM_{min}$ to $SUM_{media}$ is small, the weighting w is close to 1 and SUM term dominates in Eqn 1. The edge determination is thus almost exclusively based on intensity or SUM. In the contrasting situation where the reflectivity contrast is very poor, the ratio of $SUM_{min}$ to $SUM_{media}$ is close to 1 and the ERROR term of Eqn 1 will dominate, the edge determination then being based almost exclusively on positional information or ERROR. In-between these extremes the edge is determined by weighting SUM and ERROR appropriately in determining the edge location.

The actual locations $x_S$ and $x_E$ are determined by recording the traversing location along track 20 for each SUM and ERROR sample taken in the vicinity of the edge of the media. To avoid an excess of collected data, the SUM and the ERROR are recorded on the fly in a circular buffer until there is a step in error or a large drop in the sum. After this point, another buffer is filled to ensure that the entire edge profile has been recorded.

Post processing of the ERROR to determine $x_E$ involves examining successive samples and looking for a transition. The SUM based edge location $x_S$ is determined according to a threshold allocated using the following process:

1. If no $x_E$ was found, the threshold is set at 50% of $SUM_{media}$.
2. If $SUM_{min}$ is greater than a pre-determined value, the threshold is set at halfway between $SUM_{media}$ and $SUM_{min}$.
3. In some cases exceptions are detected such as a varying $SUM_{media}$ indicating non-uniform coating near the edge of the media or any other conditions that cause either $x_{edge}$ of $x_S$ to be unreliable. In these cases the weighting factor w is overridden to make the edge determination on the basis of solely the SUM or the ERROR signal (i.e. by setting w to zero or one).

From the above data the weighting w is calculated and then $x_{edge}$ is computed from Eqn 1.

In an alternative embodiment the positional information may be derived from the un-normalized difference between signals a and b. In such a case the edge location $x_E$ may be determined as a simple midpoint between the extremes.

As will be apparent to those skilled in the art in light of the foregoing disclosure, many alterations and modifications are possible in the practice of this invention without departing from the spirit or scope thereof. While in the embodiment depicted a specific arrangement of fixed reference stops, drum and imaging head have been shown, a person of skill in the art will readily appreciate that the principles are equally applicable in other imaging situations including systems that operate with a flat media support surface instead of a cylindrical drum. Similarly, while the algorithm has been described with reference to post processing of accumulated data the processing may be done on-the-fly should the controller have sufficient computing power to perform the necessary calculations in real time. In the described embodiments the controller is a programmable microprocessor which has the benefit of adaptability but this is not mandated. While the traversing or scanning of the beam has been indexed to displacement in the above description, a person of skill in the art will readily appreciate that if the scanning is performed at a constant known velocity the scan may be indexed to time rather than displacement.

The light source as described is an auxiliary laser diode but may be any other light source and may also be the same beam used to write the media. When using the write beam the edge detection must be done at lower power or in an inconspicuous region of the media since the possibility of marking the media obviously exists.

The position sensitive detector may also be a split sensor, well known in the art, or a CCD array and the disposition of the laser beam and PSD may vary. In some instances the incident and reflected beams may be co-axial with the reflected beam being spatially or optically separated and directed onto the PSD.

The location of the edge detection beam may be referenced by counting steps applied to a stepper motor in order to traverse a carriage on which the beam source is located. Where a motor other than a stepper motor is used a rotational encoder may be coupled to the motor to indicate the rotational disposition of the motor. Alternatively, the location may be referenced to a linear encoder such as an adhesive tape scale with corresponding read-head available from Renishaw, Gloucestershire, U.K. Furthermore, the beam may itself be scanned over the edge without traversing the source using a modulator. The modulator may be a scanning acousto-optic modulator.

What is claimed is:

1. A method for determining the location of an edge of an imaging media, the method comprising steps of:
   directing an incident beam of light towards the vicinity of the media edge such that a reflection of the incident beam is generated;
   scanning the incident beam over the media edge while monitoring the location of the incident beam in the scanning direction;
   monitoring the reflection of the incident beam to determine intensity and positional information therefrom;
   evaluating the intensity and positional information to determine of the location of the media edge; and
   wherein intensity and positional information for a plurality of beam locations is accumulated and stored as data in a computer readable memory element.

2. A method according to claim 1, wherein the evaluating step comprises examining the data to determine the relative difference in the reflection intensity between the media surface and the media support surface and calculating a corresponding weighting factor based on the relative difference, the weighting factor subsequently applied to the intensity and positional information to determine the location of the media edge.

3. A method for determining the location of an edge of an imaging media, the method comprising steps of:
   directing an incident beam of light towards the vicinity of the media edge such that a reflection of the incident beam is generated;
   scanning the incident beam over the media edge while monitoring the location of the incident beam in the scanning direction;
   monitoring the reflection of the incident beam to determine intensity and positional information therefrom;
   evaluating the intensity and positional information to determine of the location of the media edge; and
   wherein determining the positional information comprises detecting a shift in position of the reflected incident beam on a position sensitive detector as the incident beam is scanned over the media edge.

4. A system for determining the location of an edge of an imaging drum, the media secured to a media support surface, the system comprising:
   a carriage, adapted to traverse along a track, the carriage having mounted thereon:
      i) a radiation source for directing an incident beam of light towards the vicinity of the media edge;
      ii) a position sensitive detector disposed to receive a reflected beam of light from the media or support surface and to generate therefrom signals responsive to the position and intensity of the reflected beam;
   means for indicating the location of the carriage on the track;
   a controller operably connected to the detector for receiving the signals therefrom while the carriage is traversed to scan the incident beam over the media edge, the controller also being operative to analyse the signals to derive position and intensity information indicative of the location of the media edge; and
   wherein the position information comprises detection of a shift in position of the reflected beam of light on the position sensitive detector as the incident beam is scanned over the media edge.

* * * * *